(12) United States Patent
Win

(10) Patent No.: US 7,192,408 B2
(45) Date of Patent: Mar. 20, 2007

(54) PHYSICAL REHABILITATION DEVICE

(76) Inventor: Jeff Win, No.65, Tiansin Village, Yuanli Township, Miaoli County 358 (TW)

( * ) Notice: Subject to any disclaimer, the term of this patent is extended or adjusted under 35 U.S.C. 154(b) by 183 days.

(21) Appl. No.: 11/108,761

(22) Filed: Apr. 19, 2005

(65) Prior Publication Data

US 2006/0235342 A1    Oct. 19, 2006

(51) Int. Cl.
*A61F 5/00* (2006.01)
(52) U.S. Cl. ............... 602/16; 602/23; 602/26; 602/27; 601/33
(58) Field of Classification Search ............ 601/5, 601/23, 27, 33–35; 602/5, 16, 23, 24, 25, 602/26, 27
See application file for complete search history.

(56) References Cited

U.S. PATENT DOCUMENTS

| 4,620,532 | A | * | 11/1986 | Houswerth | 602/16 |
| 4,738,252 | A | * | 4/1988 | Friddle et al. | 602/16 |
| 4,982,732 | A | * | 1/1991 | Morris | 602/16 |
| 6,203,511 | B1 | * | 3/2001 | Johnson et al. | 602/16 |
| 6,993,808 | B1 | * | 2/2006 | Bennett et al. | 602/16 |
| 7,037,287 | B2 | * | 5/2006 | Cormier et al. | 602/23 |

* cited by examiner

*Primary Examiner*—Quang D. Thanh
(74) *Attorney, Agent, or Firm*—Rosenberg, Klein & Lee

(57) ABSTRACT

A physical rehabilitation device includes a first frame assembly, a second frame assembly and fixing assembly pivotally connecting the first and second frame assemblies. The fixing assembly has a pivot base on the first frame assembly and a pivot disk on the second frame assembly to be pivoted on the pivot base by a pivot member. The pivot disk has at least two lock slots with teeth on a sidewall thereof. A fixing member is pivoted on the first frame assembly, which has lock blocks associated with the lock slots respectively. The pivot base has slots associated with the lock blocks respectively to pass the lock blocks through the pivot base and to be engaged with the teeth, whereby an angle between the first frame assembly and the second frame assembly is fixed via the lock blocks engaged with the teeth.

2 Claims, 7 Drawing Sheets

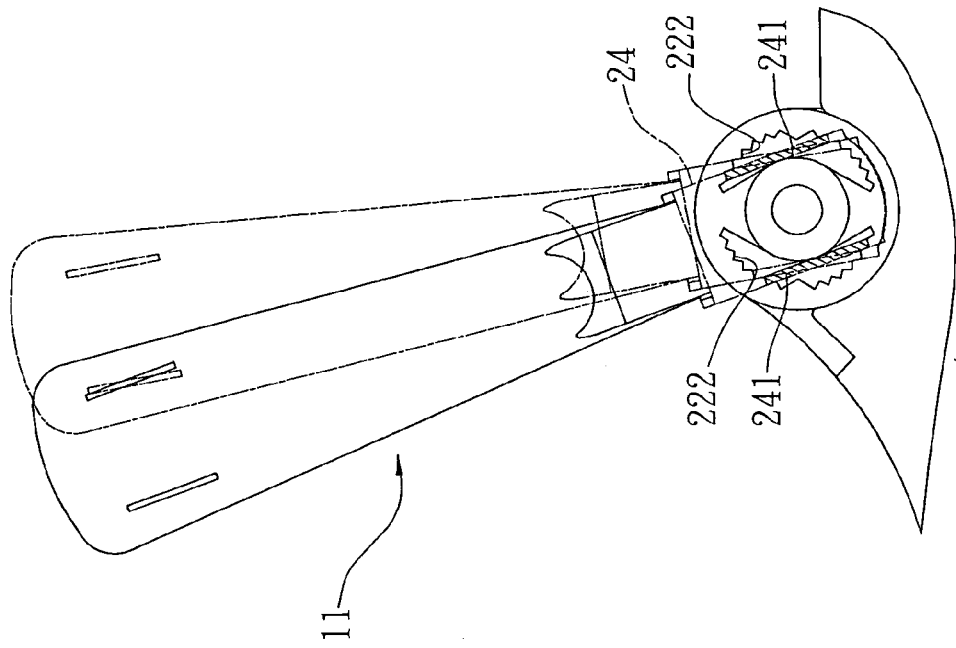
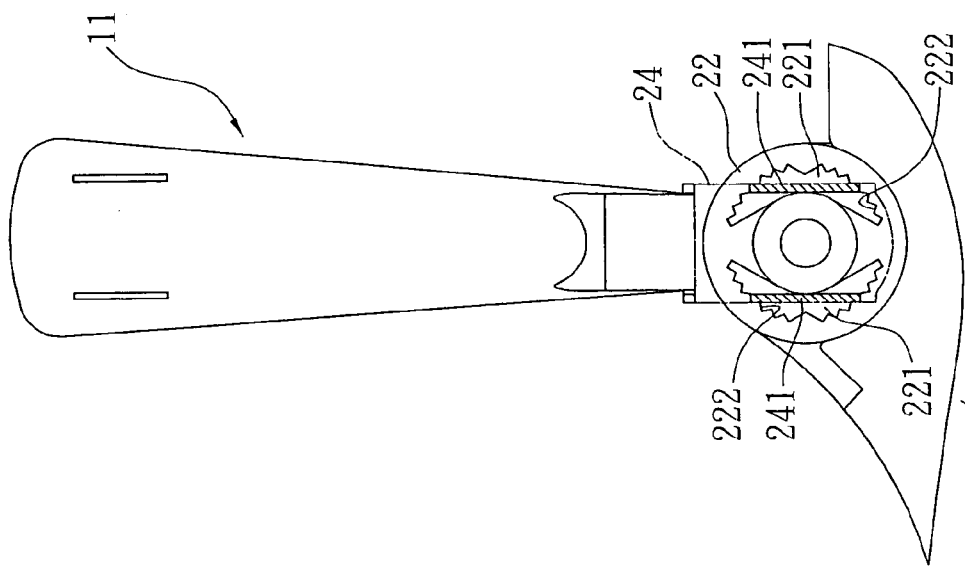

PHYSICAL REHABILITATION DEVICE

BACKGROUND OF THE INVENTION

1. Field of the Invention

The present invention relates generally to physical medicine and rehabilitation, and more particularly to a physical rehabilitation device, which angle is adjustable to support and fix body segment.

2. Description of the Related Art

FIG. 7 shows a conventional physical rehabilitation device having an upper frame assembly 81 and a lower frame assembly 82 pivoted on each other. The upper and lower frame assemblies 81 and 82 are fixed at two body segments and between the segments is a joint. In FIG. 7, the upper frame assembly 81 is fixed on the thigh, and the lower frame assembly 82 is fixed on the shank, between which is the knee joint. A fixing assembly 9 is provided at a pivot of the upper and lower frame assemblies 81 and 82 to fix the angle between the upper and lower frame assemblies 81 and 82, such that the segments and the joint are fixed by the device.

As shown in FIG. 8, the fixing assembly 9 has two fixing disks 91 on the lower frame assembly 82, between which the upper frame assembly 81 is provided. Each fixing disk 91 has a curved slot 92 with a plurality of recesses 921 on a sidewall thereof. Two blocks 93 is received in the slots 92 respective to be moved along the slots 92. Each block 93 has a movable block 931 and a post 932. The posts 932 may be received in anyone of the recesses 921 to secure the block 93. The upper frame assembly 81 is rested on the blocks 93 to be restricted at a predetermined position.

The fixing assembly 9 provides the posts 932 in the recess 921 to fix the block 93 and to fix the upper frame assembly 81 also. Some circumstance, force is concentrated on one post 932 and the post 932 is against on a sidewall of the recess 921. The strength of the fixing disk 91 at the sidewall of the recesses 932 must be stronger to prevent the fixing disk 91 from damage by the force. In practice, the distance between two neighboring recesses 932 has to be further to provide the stronger strength. As result, there are fewer angles that the upper and lower frame assemblies 81 and 82 can be adjusted.

The force exerted on one post 932 may bend it or break it also.

SUMMARY OF THE INVENTION

The primary objective of the present invention is to provide a physical rehabilitation device, which can adjust angle and has well support and fixing.

According to the objective of the present invention, a physical rehabilitation device comprises a first frame assembly and a second frame assembly pivoted on each other. A fixing assembly is provided at a pivot of the first frame assembly and the second frame assembly, which has a pivot base on the first frame assembly and a pivot disk on the second frame assembly to be pivoted on the pivot base by a pivot member. The pivot disk has at least two lock slots with teeth on a sidewall thereof, wherein the teeth are arranged on a circumference of a circle with the pivot member to be a center of the circle. A fixing member is pivoted on the first frame assembly, which has lock blocks associated with the lock slots respectively to be engaged with anyone of the teeth. The pivot base has slots associated with the lock blocks respectively to pass the lock blocks through the pivot base and to be engaged with the teeth, whereby an angle between the first frame assembly and the second frame assembly is fixed via the lock blocks engaged with the teeth.

BRIEF DESCRIPTION OF THE DRAWINGS

FIG. 3 is a sectional view in part of the first preferred embodiment of the present invention;

FIG. 5 is a perspective view of the first preferred embodiment of the present invention, showing a person wearing the rehabilitation shoe;

DETAILED DESCRIPTION OF THE INVENTION

Figure 1:
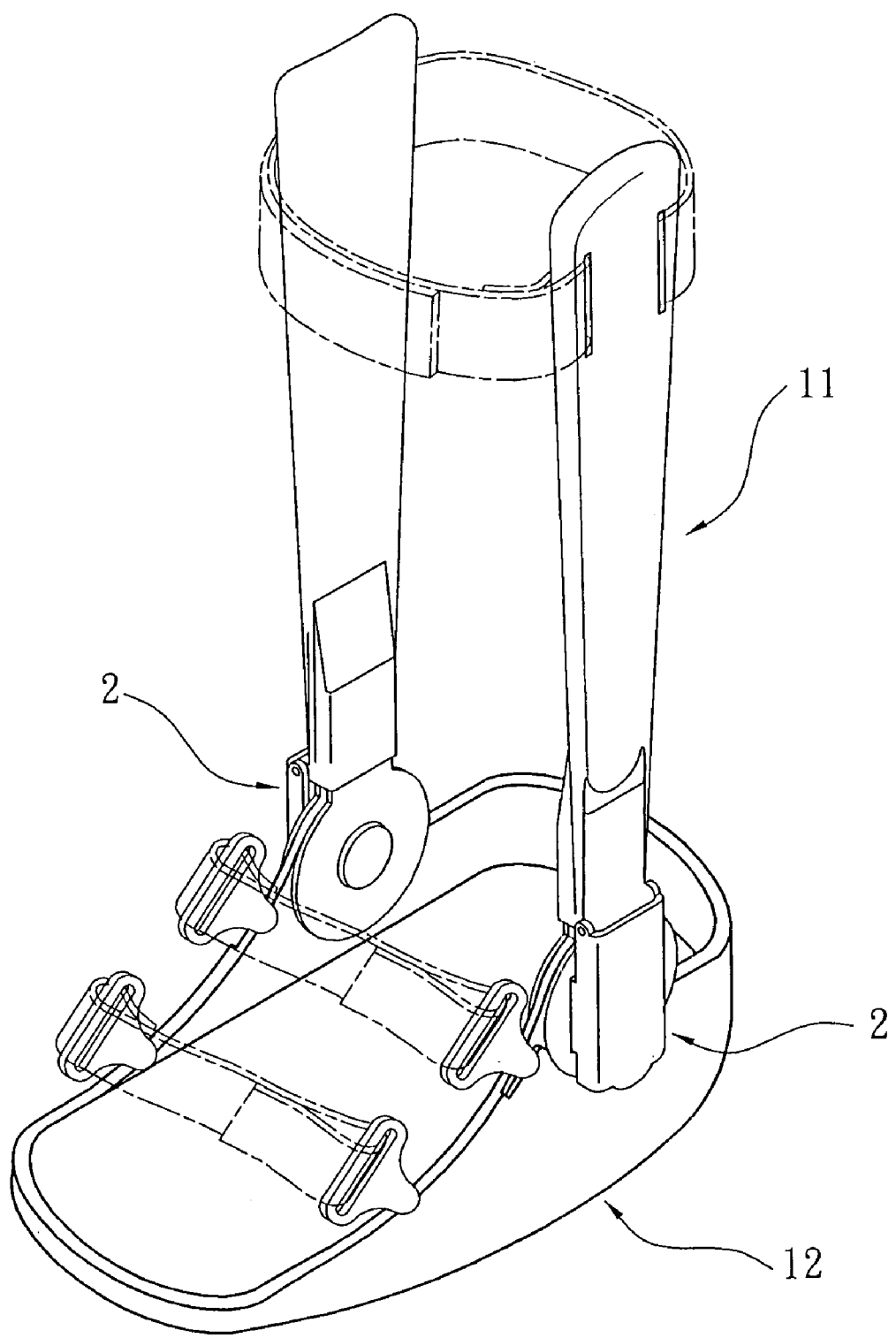
FIG. 1 is a perspective view of a first preferred embodiment of the present invention, showing the rehabilitation shoe.

As shown in FIGS. 1 to 4, a rehabilitation device of the first preferred embodiment of the present invention is a rehabilitation shoe. As shown in FIG. 1, the shoe has a first frame assembly 11 (the shank frame) and a second frame assembly 12 (the sole) pivoted on each other. The first and second frame assemblies 11 and 12 are fixed on two jointed body segments, such as foot and shank. A fixing assembly 2 is provided at a pivot of the first and second frame assemblies 11 and 12 to fix an angle between the first and second frame assemblies 11 and 12.

Figure 2:
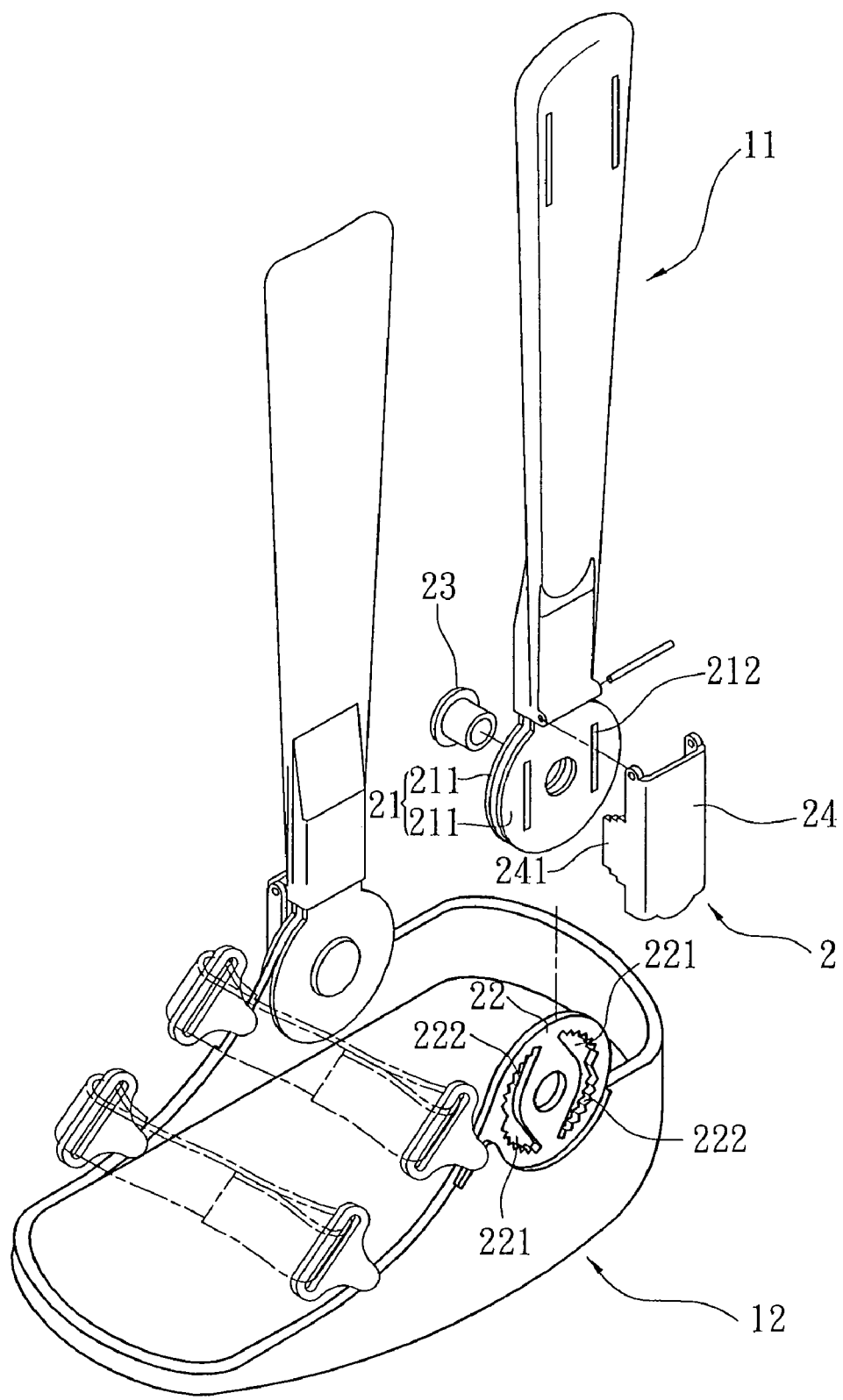
FIG. 2 is an exploded view of the first preferred embodiment of the present invention.
Figure 4:
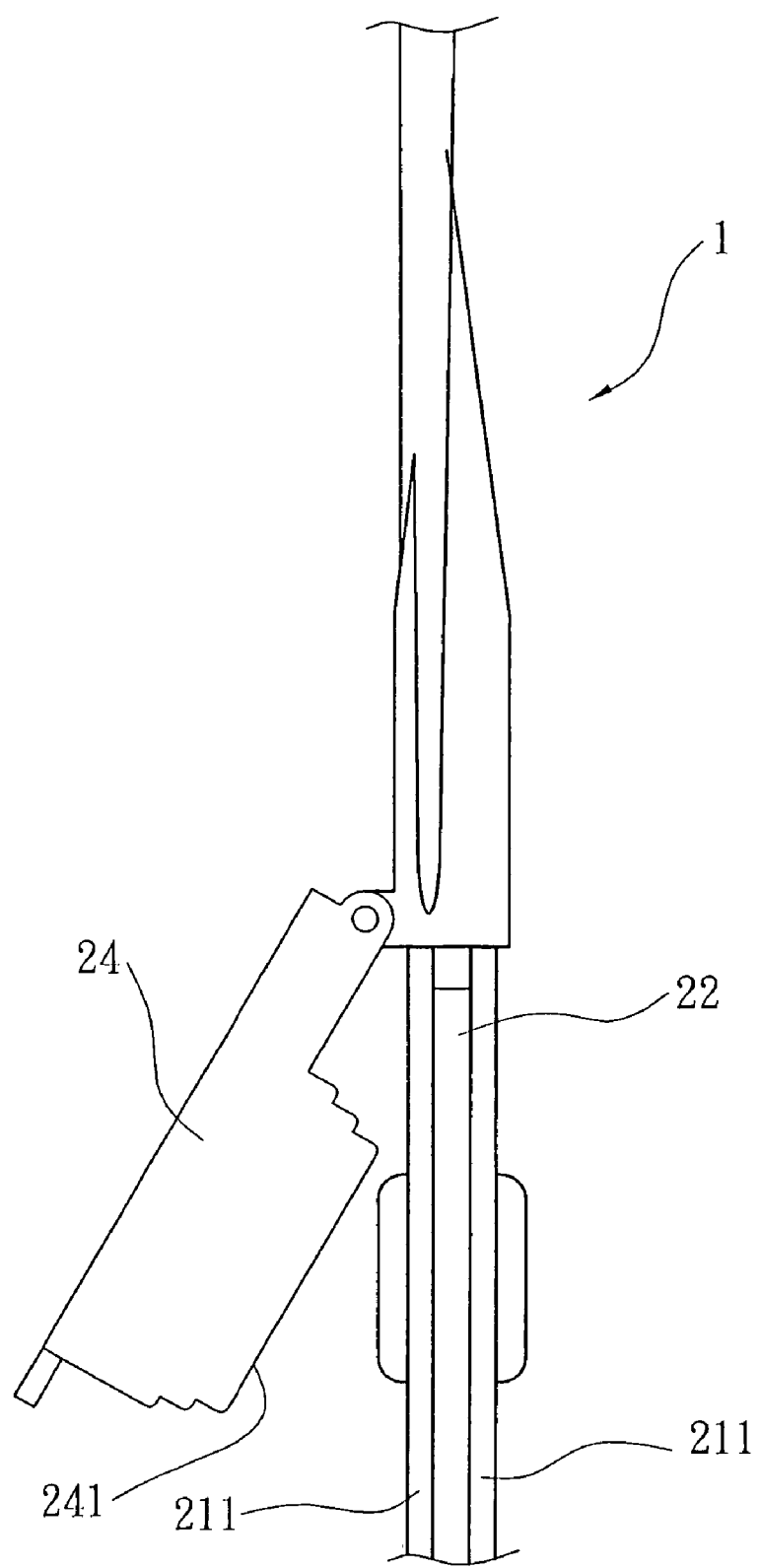
FIG. 4 is a sketch diagram of the fixing member of the first preferred embodiment of the present invention.

As shown in FIG. 2 to FIG. 4, the fixing assembly 2 includes a pivot base 21 on the first frame assembly 11 and a pivot disk 22 on the second frame assemblies 12. The pivot base 21 has two parallel plates 211, between which the pivot disk 22 is received. A pivot member 23 connects the pivot base 21 and the pivot disk 22. The pivot disk 22 has two lock slots 221, each of which has teeth 222 on a sidewall thereof. The teeth 222 are arranged on a circumference of a circle with the pivot member 23 to be the center of the circle. The first frame assembly 11 is pivoted with a fixing member 24 with two lock blocks 241 associated with the lock slots 221 to be engaged with anyone of the teeth 222. The pivot base 21 is provided with two slots 212 on the plates 211 associated with the lock blocks 241 respectively to pass the lock blocks 241 through the plates 211 and to be engaged with anyone of the teeth 222.

As shown in FIG. 3 and FIG. 5, the lock blocks 241 have opposite ends engaged with four of the teeth 222, such that a force of the first and second frame assemblies 11 and 12 is shared by the four teeth 222. Therefore, the rehabilitation device of the present invention can sustain greater force than the conventional device.

In addition, the teeth 222 are arranged on the circumference with the pivot member 23 to be the center, such that a sufficient width between an edge of the pivot disk 22 and the lock slots can take greater force. Except that, the force is shared by four teeth 222, such that a distance between the neighboring teeth 222 can be narrowed, and the teeth 222 still have sufficient strength to take the force. As a result, the angle between first and second frame assemblies 11 and 12 can be adjusted in a fine angle, as shown in FIG. 5.

In conclusion, the rehabilitation device of the present invention can provide a fine angle adjustment and a well support and fixing of the segments.

Figure 6:
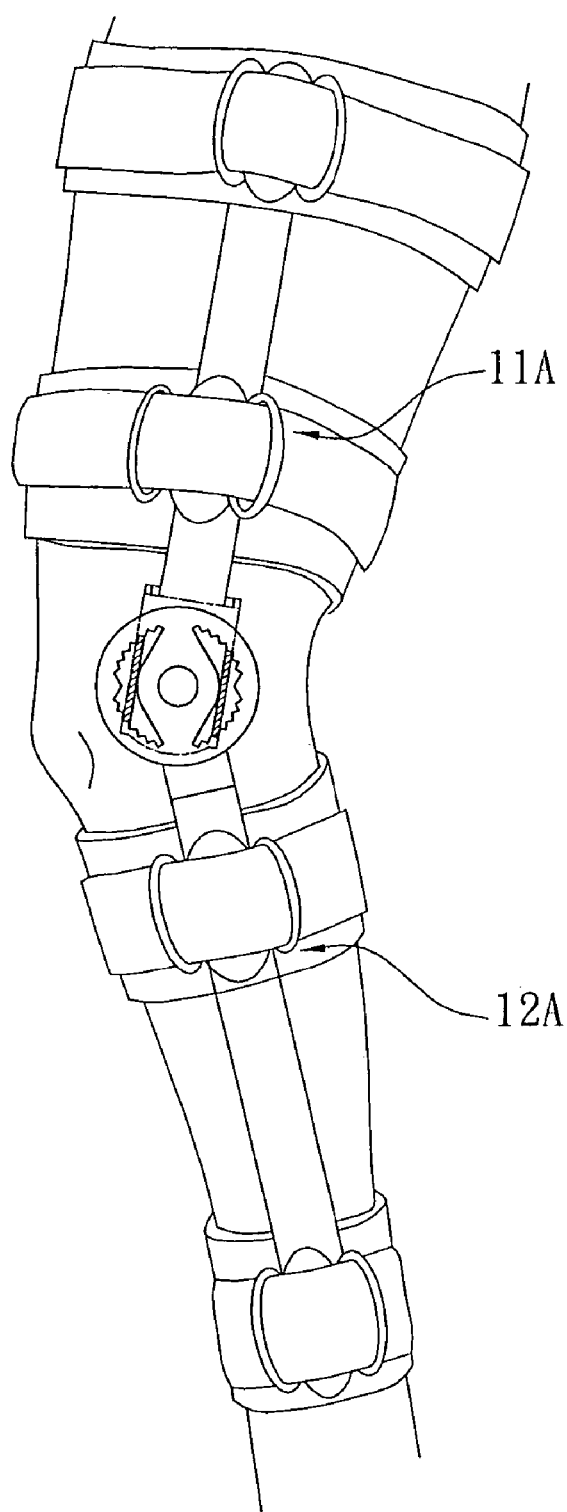
FIG. 6 is a perspective view of a second preferred embodiment of the present invention, showing a person wearing the rehabilitation device.
Figure 7:
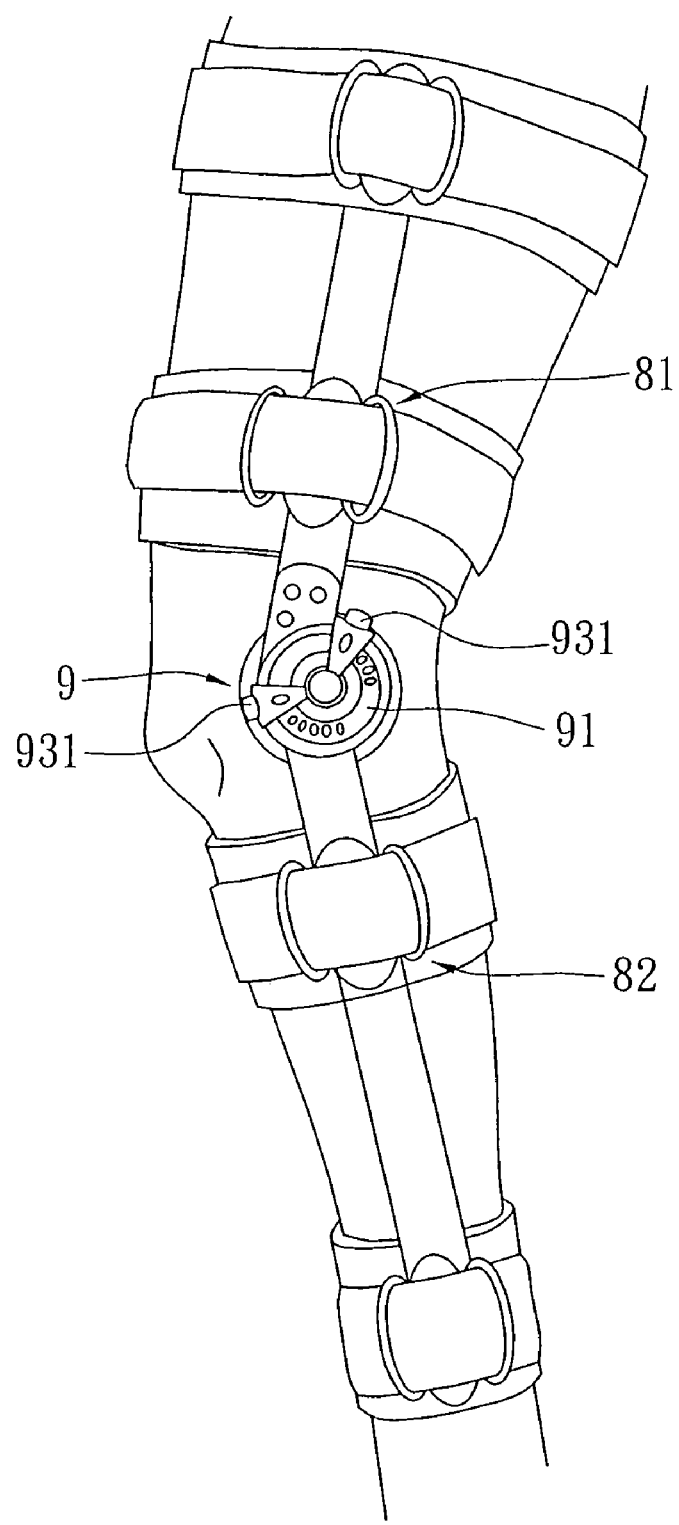
FIG. 7 is a perspective view of the conventional rehabilitation device.
Figure 8:
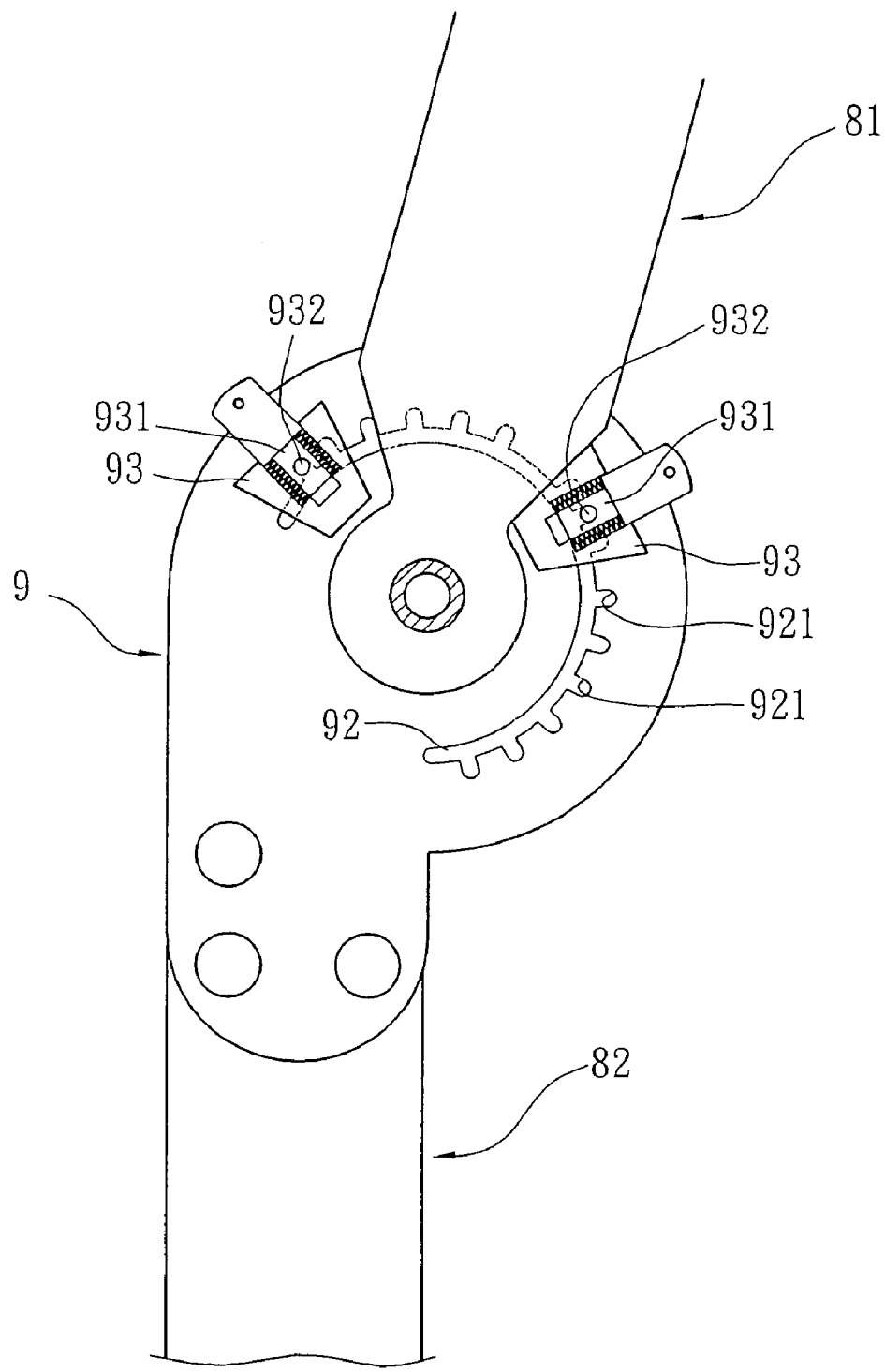
FIG. 8 is a sketch diagram of the fixing assembly of the conventional rehabilitation device.

As shown in FIG. 6, a rehabilitation device of the second preferred embodiment of the present invention, which is similar to the rehabilitation device of the first preferred embodiment, except that a first frame assembly 11A and a second frame assembly 11B is designated to be fixed on the thigh and the shank respectively. In practice, the first and second frame assemblies can be designated to be fixed on any two jointed segments, such as upper arm and forearm or forearm and palm (not shown) that can achieve the scope of the present invention also.

What is claimed is:

1. A physical rehabilitation device, comprising a first frame assembly and a second frame assembly pivoted on each other, wherein the first frame assembly and the second frame assembly are adapted to be fixed on two jointed segments respectively; a fixing assembly provided at a pivot of the first frame assembly and the second frame assembly, which has a pivot base on the first frame assembly and a pivot disk on the second frame assembly to be pivoted on the pivot base by a pivot member; the pivot disk having at least two lock slots with teeth on sidewalls thereof, wherein the teeth are arranged on a circumference of a circle with the pivot member to be a center of the circle; a fixing member pivoted on the first frame assembly, which has lock blocks associated with the lock slots respectively to be engaged with anyone of the teeth; the pivot base having slots associated with the lock blocks respectively to pass the lock blocks through the pivot base and to be engaged with the teeth, whereby an angle between the first frame assembly and the second frame assembly is fixed via the lock blocks engaged with the teeth.

2. The physical rehabilitation device as defined in claim 1, wherein the pivot base has two plates, between which the pivot disk is received, and the slots are provided on the plate respectively.

* * * * *